United States Patent [19]

Bouma

[11] Patent Number: 4,597,121
[45] Date of Patent: Jul. 1, 1986

[54] INFANT COVER WITH RECEIVING POUCH

[76] Inventor: Juliette A. Bouma, P.O. Box 282, Augusta, Mont. 59410

[21] Appl. No.: 600,010

[22] Filed: Apr. 13, 1984

[51] Int. Cl.$^4$ .............................................. A47G 9/00
[52] U.S. Cl. ............................................. 5/494; 2/69; 5/413
[58] Field of Search .................. 5/494, 413, 485, 482, 5/424; 2/69, 69.5, 403, 406 (U.S. only)

[56] References Cited

U.S. PATENT DOCUMENTS

| 2,461,749 | 2/1949 | Mallette | 5/494 |
| 2,854,669 | 10/1958 | Cohen | 2/403 |
| 2,931,043 | 4/1960 | Achner | 2/69.5 |
| 2,989,753 | 6/1961 | Burner | 2/69.5 |
| 3,963,022 | 6/1976 | Rotello | 2/403 |
| 4,172,300 | 10/1979 | Miller | 5/494 |

FOREIGN PATENT DOCUMENTS 1949351 7/1967 France ........................................ 2/69
324146 9/1957 Switzerland ............................. 5/494

Primary Examiner—Alexander Grosz
Attorney, Agent, or Firm—McCord & McCord

[57] ABSTRACT

A cover for an infant or small child having a pouch attached thereto for receiving the legs and lower torso of the child. The pouch is oriented diagonally so as to be substantially in alignment with opposite corners of the cover and is secured to the central portion of the cover by double-stitching along the sides and the crotch area thereof. The pouch is equipped with a zipper to facilitate inserting the child into and removing the child from the pouch and a drawstring is received within a pocket sewn into the waist portion of the pouch to adjust the pouch to fit the individual child. The cover may be fabricated from a lightweight cotton flannel material for warmer weather or a heavier quilted material for cooler weather. Different fabrics may be used for the inner and outer portions of the cover.

8 Claims, 12 Drawing Figures

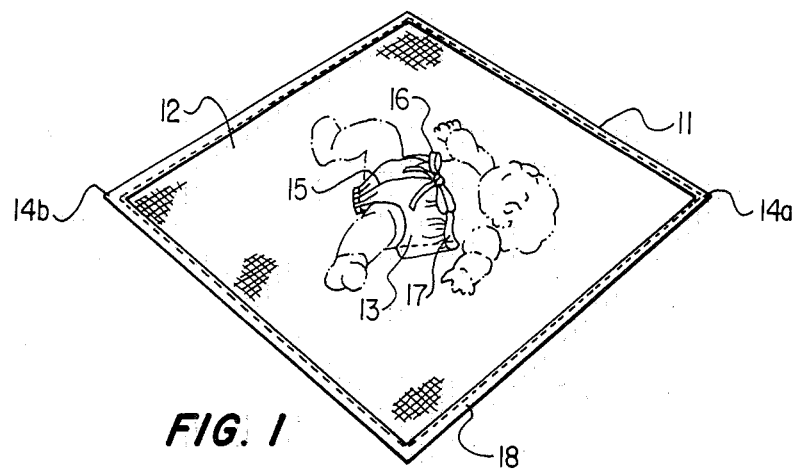
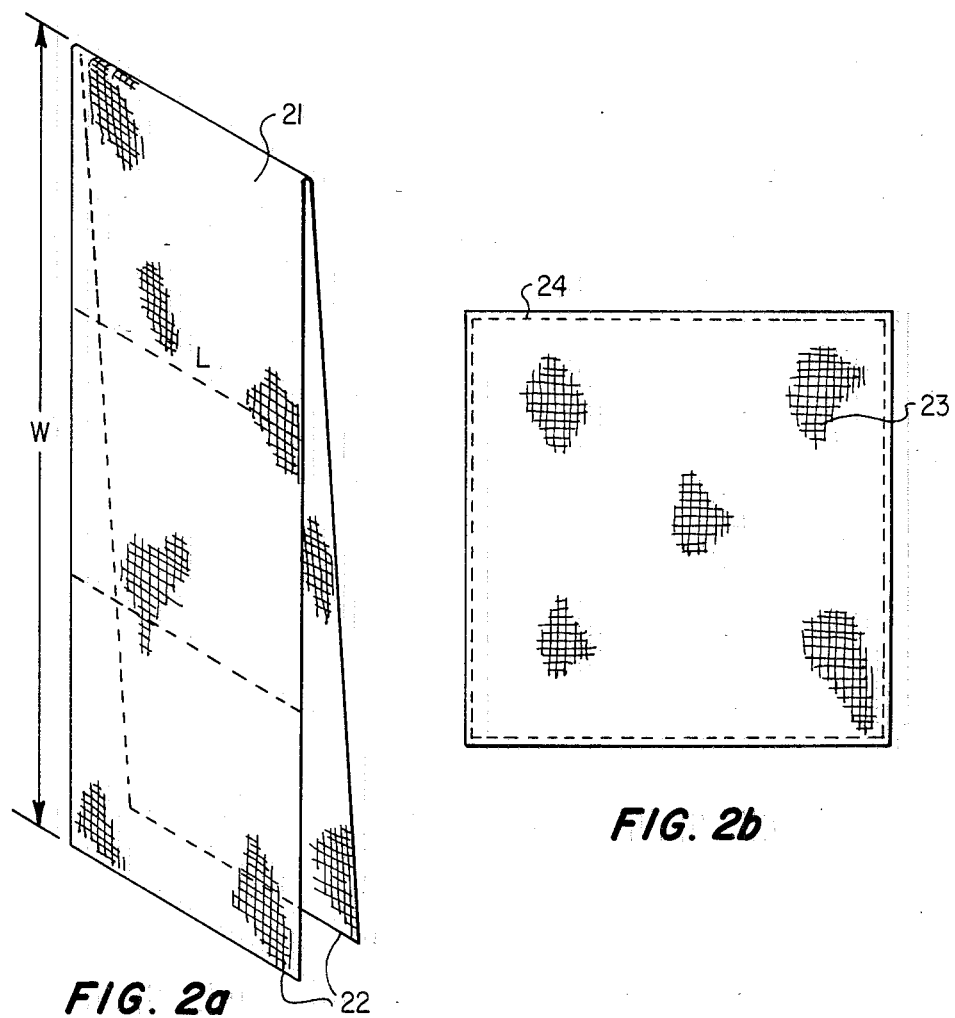

INFANT COVER WITH RECEIVING POUCH

BACKGROUND OF THE INVENTION

1. Field of the Invention

This invention relates to covers for infants and small children and in particular to a cover having a pouch attached thereto for receiving the legs and lower torso of a child.

2. Description of the Prior Art

Blankets and other coverings for infants are well known in the art. One example of an infant cover is the so-called pouch carrier, which includes waist and shoulder straps for being fitted around the parent's waist and shoulders and a pouch in which the infant is received so that only the top of the baby's head is exposed. The pouch may be positioned against either the front or the back portion of the parent's torso. These pouch carriers are convenient for transporting an infant from place to place, but it is often difficult to comfortably position the child within the pouch. Also, the pouch carrier is not suitable for infants beyond the age of approximately three (3) months because of the constraints on the child's movement.

Other types of infant covers are shown in U.S. Pat. Nos. 2,140,797; 2,374,712; and 2,419,989; and in Swiss Pat. No. 324,416. U.S. Pat. No. 2,140,797 shows a bed jacket attached to a blanket. Both the blanket and the jacket are opened by means of a zipper for enveloping the child therein, the bed jacket for covering the child's torso and arms. U.S. Pat. No. 2,374,712 teaches a body garment which is attached at the crotch portion thereof to a bed cover. The body garment includes a body portion with openings therein for a child's arms and legs and the cover includes strings for attachment to a crib or the like. U.S. Pat. No. 2,419,989 teaches a bed jacket attached to a blanket by means of tie strings. The blanket includes a T-shaped opening through which the child is placed onto the bed cover and tie strings for securing the bed cover to the crib. The jacket is then placed on the child and tied to the bed cover to provide a protective covering for the child. Swiss Pat. No. 324,146 shows a sleeping blanket with a harness attached thereto and a pair of short pants which can be snapped onto the blanket adjacent to the shoulder harness for receiving the child's torso and legs. The blanket further includes tie straps for the purpose of securing it to a bed.

The above described references are directed to sleeping blankets for use in a baby crib only and are not suitable for use as receiving blankets whereby an infant may be kept warm while being transported. Furthermore, the sleeping blankets in the above described references severely limit the freedom of movement of the child and are suitable for use only when the child is in a sedentary state, such as while asleep. Nor is there any teaching or suggestion as to whether or how the various body covers shown in the references may be adjusted to fit the size of the particular child.

OBJECTS OF THE INVENTION

It is one object of the present invention to provide an improved cover for an infant or small child.

It is another object of the invention to provide a receiving blanket for an infant or small child which will not slip up and down, relative to the position of the child as the child moves within the blanket.

It is yet another object of the invention to provide a receiving blanket for an infant or small child in which the child may be held in a secure position, while allowing the child freedom to move within the blanket.

It is a further object of the invention to provide a cover for an infant or small child having a pouch attached thereto for receiving the legs and lower torso of the child, the pouch being adjustable to fit the child.

SUMMARY OF THE INVENTION

These and other objects are accomplished in accordance with the present invention. A cover for an infant or small child having a pouch member attached thereto for receiving the legs and lower torso of the child is provided. The pouch member is oriented diagonally with respect to the substantially rectangular shape of the cover so that the pouch member is substantially in alignment with opposite corners of the cover.

In one embodiment the pouch member is equipped with a zipper to facilitate inserting the child into and removing the child from the pouch member. A drawstring is received within a casing member attached to the waist portion of the pouch member to adjust the size of the pouch member to fit the individual child. In another embodiment a second drawstring is received within a second casing member which is attached to selected portions of adjacent edges of the cover to provide a head covering for the child when opposite ends of the second drawstring are pulled together In yet another embodiment, a third drawstring is received within a third casing pocket which extends substantially along the entire length of adjacent edges of the cover to envelope a portion of the cover around the torso and legs of the child. Alternatively, a pair of female snap members are disposed adjacent to respective opposite first and second corners of the cover and complementary first and second male snap members are disposed on a third corner of the cover for engaging the female snap members to hold the first, second and third corners of the cover in position around the child.

in a preferred embodiment, the pouch member is secured to central portion of the cover and includes an opening at the top portion thereof through which the child may be inserted into the pouch member and a pair of openings at the lower portion thereof through which the child's legs may be inserted. The cover may be fabricated from a lightweight cotton flannel for warmer weather or, alternatively, from a heavier quilted material for cooler weather. The cover and the pouch may be fabricated from the same material or from coordinated fabrics. Different materials may be used on the inside and on the outside of the cover. For example, a soft cotton flannel material on the inside of the cover provides the best comfort for the child, whereas a more durable polyester-cotton, denim or corduroy material is preferable for the outside of the cover.

DESCRIPTION OF THE DRAWINGS

FIG. 1 is a front elevational view of a first embodiment of the infant cover of the present invention, which includes a pouch attached to the central portion thereof in which an infant is positioned;

FIG. 2a is a perspective view of the folded material from which the infant cover of the present invention is fabricated;

FIGS. 2b–2d are various elevation views illustrating the fabrication of the blanket member of the infant cover;

DETAILED DESCRIPTION OF A PREFERRED EMBODIMENT

Figure 2C:
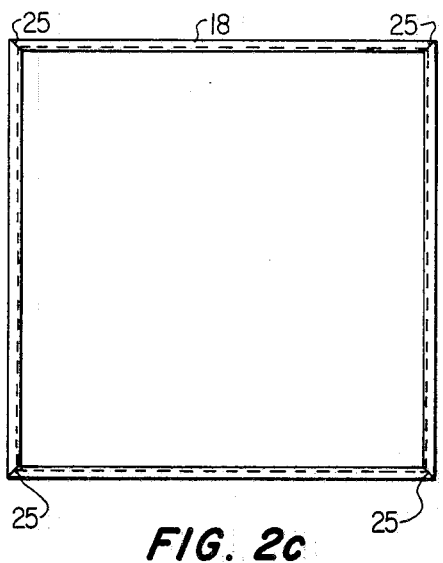

Referring to FIG. 1, infant cover 11 is comprised of a substantially square-shaped blanket 12, with each of the four edges of blanket 12 being approximately forty-five (45) inches in length. Attached to blanket 12 at the central portion of the inner surface thereof, (i.e., the surface which is in contact with the child when the child is wrapped in cover 11) is a pouch member 13, which is substantially in the shape of a pair of short pants. Pouch member 13 is oriented diagonally with respect to blanket 12 so as to be substantially in alignment with opposite corners 14a and 14b in order to facilitate wrapping cover 11 around the child for optimum protection and warmth.

Pouch member 13 includes a zipper member 15 extending vertically along the front portion thereof to facilitate placing the child into and pulling the child out of pouch member 13 and a drawstring 16, which is received within a casing 17 sewn into the waist portion of the pouch member 13 to adjust the size of pouch member 13 to fit the individual child. A bias tape 18 is sewn around the perimeter of blanket 12 to strengthen the border and corners of cover 11.

Referring to FIG. 2a, a predetermined length L of material 21, having a width W of approximately 45 inches is folded so that the "wrong" sides (i.e. the non-ornamental or non-patterned side of the fabric) are together and selvages 22 are in contact. If the inner and outer surfaces to cover 11 are to be formed from the same fabric, two pieces, each of which is 45 inches in length, are cut from folded material 21 to form two square-shaped pieces having a length of approximately 45 inches along each edge thereof for the inner and outer surfaces of cover 11. If it is desired to use different fabrics for the inner and outer surfaces of cover 11, a 45 inch length is cut from each fabric, which is folded as described above, to form two square-shaped pieces of different fabrics for the inner and outer surfaces of cover 11.

Figure 2D:
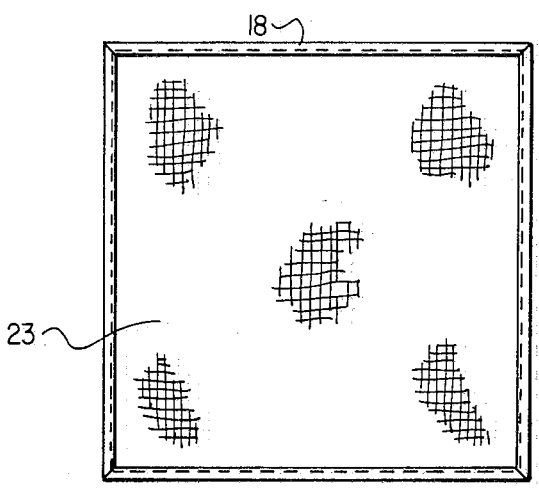

To form blanket 12, the two pieces of fabric cut from material 21, as described above, are placed in contact with the "wrong" sides of each piece and the respective edges thereof in contact, so that "right" sides 23 of each piece are exposed. The two pieces are then stitched together along all four edges using a basting stitch 24, as shown in FIG. 2b. As shown in FIG. 2c, the corners of bias tape 18 are then marked to correspond with the respective corners of blanket 12 and bias tape 18 is turned to expose the "wrong" side thereof and is stitched with a diagonal stitch at corners 25 thereof to "finish" corners 25 before stitching bias tape 18 to blanket 12, thereby reinforcing the strength of the corners of cover 11. Bias tape 18 is then placed over the respective edges of blanket 12 and stitched thereto using a decorative stitch if desired, as depicted in FIG. 2d.

Referring to FIGS. 3a–3d, pouch member 13 is formed using appropriate patterns for the left and right "legs" of pouch member 13 and for drawstring 16 and drawstring casing 17. The patterns for pouch member 13 are cut from a fabric material, which may be the same as or different from material 21 used to fabricate blanket 12. Similarly, different fabrics may be used for the inner and outer surfaces of pouch member 13. For example, a soft cotton or cotton flannel material may be used for the inner surface of pouch member 13 to provide extra comfort for the child, while a more durable material such as corduroy may be used on the outer surface.

Zipper member 15 is then sewn into the respective right and left "legs" 31 and 32 of pouch member 13 by stitching the respective inner and outer surfaces of both right and left "legs" 31 and 32 of pouch member 13 along the length of zipper member 15, with the respective "right" sides of the inner and outer surfaces in contact and zipper member 15 sandwiched therebetween. With the "right" sides of the inner surface material in contact with each other and the "right" sides of the outer surface material in contact with each other, crotch area 33 of pouch member 13 is stitched below zipper member 15, and pouch member 13 is "turned" to expose the "right" sides of the material, the outer surface of pouch member 13 being shown in FIG. 3a.

Figure 3A:
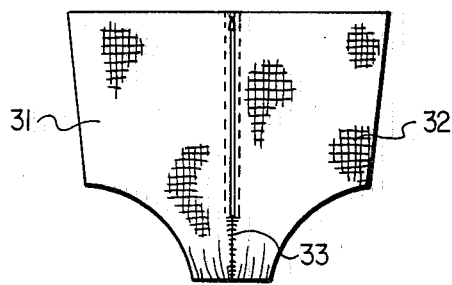
FIGS. 3a–3d are various elevational views illustrating the formation of the pouch member of the infant cover.
Figure 3B:
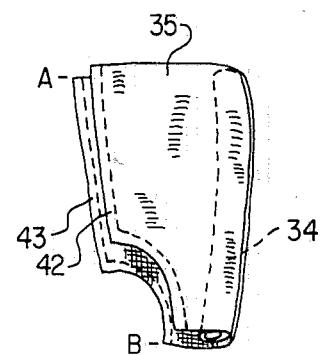

The edges of the inner and outer surfaces of pouch member 13 are sewn together by first rolling left "leg" 32 of pouch member 13 into a roll 34 and folding roll 34 onto right "leg" 31. The inner surface of right "leg" 31 is folded over roll 34 so that "right" sides 23 of the material are in contact and "wrong" sides 35 are exposed, as shown in FIG. 3b. Edges 42 and 43 of the respective outer and inner surfaces of pouch member 13 are then sewn together along the dotted lines between points A and B. Left "leg" 32 is then turned to expose "right" sides 23 of left "leg" 32 and the above procedure is then repeated for right "leg" 31.

Figure 3C:
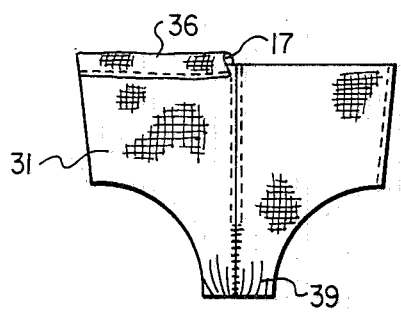
Figure 3D:
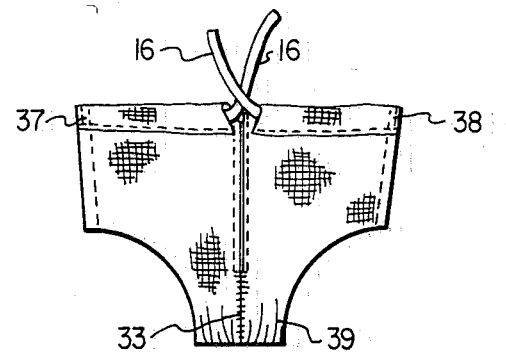

Referring to FIGS. 3c and 3d, drawstring 16 and drawstring casing 17 are attached as follows. "Right" side 36 of the casing material is placed in contact with the "right" side of the outer surface of "right" leg 31 of pouch member 13, so that the "wrong" side of casing 17 is exposed. The casing material is stitched to the outer surface of right "leg" 31 leaving a 6/8 inch seam at the top. The casing material is then folded over the top of right "leg" 31 to expose "right" side 36 and is stitched to the inner surface of right "leg" 31 to form drawstring casing 17 along the top of the waist portion of the pouch member 13. The above procedure is then repeated on left "leg" 32 of pouch member 13. Individual drawstrings 16 are then inserted into the respective casings 17 and are stitched to respective ends 37 and 38 thereof to secure drawstrings 16 within their respective casings 17. As an additional feature, pleats 39 are formed in crotch area 33 of pouch member 13 by folding pleat allowances towards zipper member 15 and baste-stitching along the bottom portion of the pleats to hold the pleats in place. Pleats 39 prevent the crotch from "bunching up" between the legs of the child and causing the child discomfort.

Figure 4:
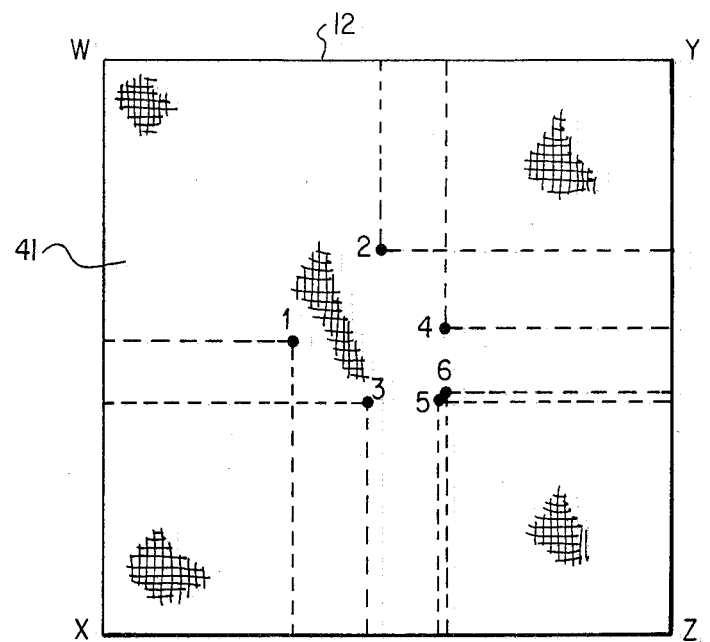
FIG. 4 is an elevational view of the blanket member of the infant cover indicating the points at which the pouch member is attached to the blanket member.

Once pouch member 13 has been fabricated, the next step is to attach pouch member 13 to cover 11. As shown in FIG. 4, six points are located on the inner surface 41 of blaket 12 for properly locating pouch member 13. Points 1 and 2, which represent the opposite edges of the waist or top portion of pouch member 13 are located by measuring 22 inches from corner W along edges W-X and W-Y, respectively, and then measuring 15 inches inwardly. Points 1 and 2 are 23 inches from edges X-Z and Y-Z, respectively. Points 3 and 4 which represent the points on the opposite edges of pouch member 13 where the edges begin to curve inwardly, are located by measuring 21 inches inward from respective edges W-X and W-Y and 18½ inches inwardly from respective edges X-Z and Y-Z, the intersections of the respective measuring lines being the locations of points 3 and 4. Points 5 and 6, which are at the outer edges of the crotch area 33 of pouch member 13, are respectively located at the intersections of lines measured 18½ inches inwardly from respective edges X-Z and Y-Z and 19 inches inwardly from respective edges Y-Z and X-Z.

After the attachment points have been located, pouch member 13 is positioned on blanket 12 with the inner surface thereof exposed and the bottom edge of crotch area 33 in alignment with points 5 and 6. Crotch area 33 is then stitched at least three times along a line which is approximately ⅜ inch from the bottom edge thereof. Pouch member 13 is then turned over so that its outer surface is exposed and its edges are positioned along the respective lines between points 1 and 3 and points 2 and 4 and crotch portion 33 is stitched again at least three times along a line which is approximately ⅜ inch from the previous seam. The edges of pouch member 13 are stitched along respective lines 52a and 52b (see FIG. 5), which are approximately ⅜ inch inward from the respective edges thereof to reinforce the attachment of pouch member 13 along the top and side seams.

Figure 5:
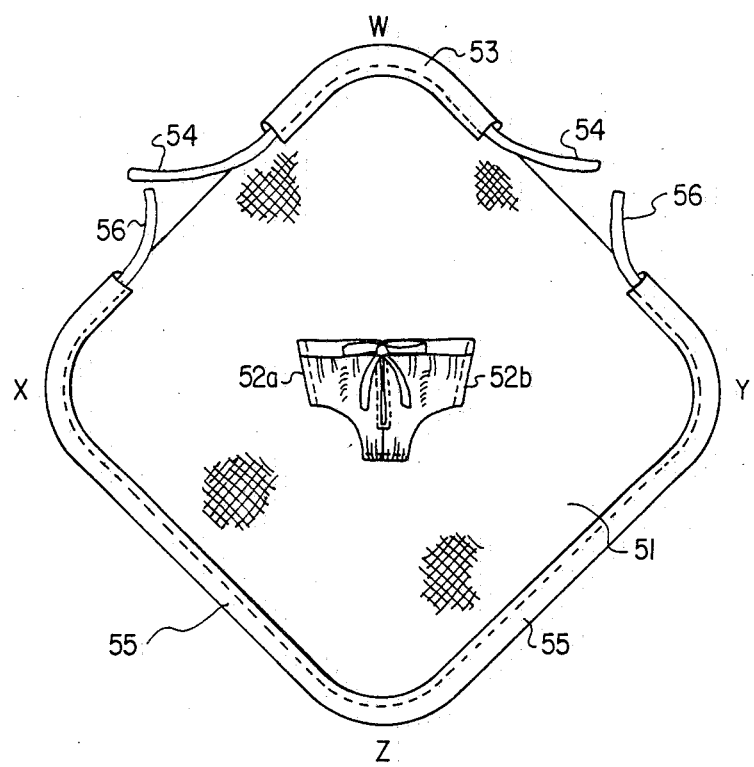
FIG. 5 is an elevational view of a second embodiment of the infant cover of the present invention.
Figure 6:
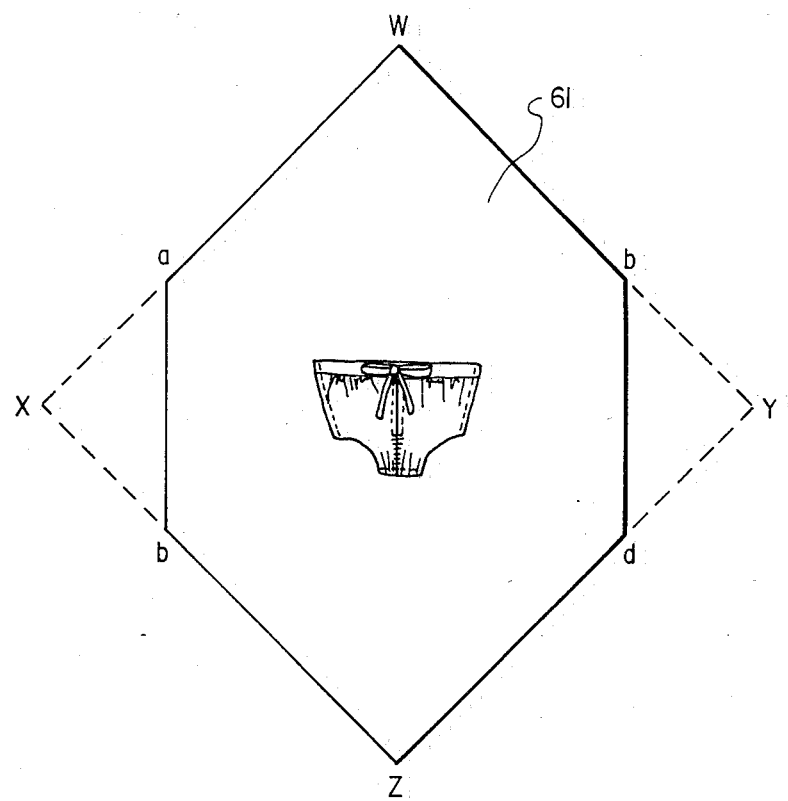
FIG. 6 is an elevational view of a third embodiment of the infant cover of the present invention.

Other embodiments of the infant cover of the present invention are depicted in FIGS. 5 and 6. FIG. 5 shows a substantially rectangular cover 51 having rounded corners. A drawstring casing 53 may be sewn along the border of cover 51, extending partially along line X-W, around rounded corner W and partially along line W-Y, for receiving a drawstring 54 therein to provide a "hood" type covering for the child's head when the ends of drawstring 54 are pulled and tied together. In addition, another drawstring casing 55 may be sewn along the border of cover 51, extending along lines Z-X and Z-Y and partially along lines X-W and Y-W, for receiving drawstring 56, the ends of which may be attached to envelope the torso and legs of the child in a "sleeping bag" arrangement. As an alternative to the drawstring and casing arrangement, complementary snaps (not shown) may be disposed on corners X, Y and Z for securing the bottom portion of cover 11 when covers X and Y are folded over the child and corner Z is folded up and over over corners X and Y. In yet another embodiment, as illustrated in FIG. 6, cover 11 may be cut along lines a-b and c-d to form a substantially hexagonal-shaped cover 61 and a separating zipper sewn along lines a-b and c-d to secure cover 61 around the child.

Covers 11, 51 and 61 and pouch member 13 may be fabricated from the same material or from color-coordinated fabrics. In addition, different materials may be used for the inner and outer surfaces of both cover 11 and pouch member 13. For example, a soft cotton flannel material may be used on the inside of cover 11 for the child's comfort, while a more durable polyester-cotton, denim or corduroy material is suitable for the outer surface of cover 11. For warm weather use, a lightweight cotton material is preferable, while a quilted material is preferable for cooler weather.

Although a preferred embodiment of the invention has been described in detail it should be understood that various changes, alterations and substitutions can be made therein without departing from the spirit and scope of the invention as defined by the appended claims.

What is claimed is:

1. A cover for enveloping an infant or small child, said cover having a fabric section attached to a central portion thereof, said fabric section comprising:
   an upper edge, first and second oppositely positioned side edges extending substantially orthogonally with respect to said upper edge and first and second curved lower edges extending downwardly from respective first and second side edges and converging to form a third lower edge at a lowermost portion of said fabric section, said third lower edge being substantially parallel with said upper edge;
   said fabric section being attached to said cover along substantially the entire respective lengths of said first and second side edges and along substantially the entire width of said third bottom edge, the attachment of said fabric section to said cover defining a pouch member for receiving the legs and lower torso of a child;
   said upper edge further including a casing member attached along substantially the entire length thereof, said casing member having a drawstring partially disposed therein, and a plurality of pleat members disposed adjacent to said third lower edge to prevent the material of the fabric section from bunching up around the child's crotch when the child is placed in the pouch member.

2. The cover according to claim 1 wherein said upper edge of said fabric section cooperates with said cover to provide a first opening for receiving the legs and lower torso of the child and said second and third lower edges of said fabric section cooperate with said cover to define respective second and third openings for receiving respective ones of the child's legs.

3. The cover according to claim 2 further including a zipper member attached to a central portion of said fabric section, said zipper member extending along substantially the entire length of said fabric section from said upper edge to a position adjacent to said third bottom edge, said zipper member for facilitating the insertion of the child into and the removal of the child from the pouch member.

4. The cover according to claim 1 wherein said cover has a substantially rectangular shape and wherein said fabric section is oriented diagonally with respect to the cover so that the upper edge of said fabric section is substantially in alignment with opposite corners of the cover.

5. The cover according to claim 1 wherein said cover has rounded corners and includes a second casing member extending around a first one of said rounded corners and at least partially along first and second adjacent edges of said cover and a second drawstring partially disposed within said second casing member, for enveloping a portion of the edges of the cover to which the casing is attached to provide a head covering for the child.

6. The cover according to claim 5 further including first and second female snap members respectively disposed adjacent to respective first and second opposite corners of the cover and first and second complementary male snap members disposed on a third corner of the cover engaging said first and second female snap members to envelope the child within the cover.

7. The cover according to claim 5 further including a third casing member extending around a second one of said rounded corners opposite from said first rounded corner and substantially along third and fourth adjacent edges of said cover and a third drawstring partially disposed within said third casing member, for enveloping the cover around the torso and legs of the child.

8. The cover according to claim 1 wherein said cover has a substantially hexagonal shape and includes zipper means having first and second members attached to said cover and extending along first and second opposite edges thereof, said first and second opposite edges forming obtuse angles with the respective edges which are adjacent to said first and second opposite edges, for enveloping the child within the cover when the first and second members of the zipper means are engaged.

* * * * *